United States Patent [19]
May

[11] Patent Number: 5,650,541
[45] Date of Patent: Jul. 22, 1997

[54] ETHACRYNIC ACID-LIKE COMPOUNDS AND USE THEREOF TO TREAT GLAUCOMA

[75] Inventor: Jesse A. May, Fort Worth, Tex.

[73] Assignee: Alcon Laboratories, Inc., Fort Worth, Tex.

[21] Appl. No.: 583,928

[22] Filed: Jan. 11, 1996

Related U.S. Application Data

[62] Division of Ser. No. 49,215, Apr. 19, 1993, Pat. No. 5,506,226.

[51] Int. Cl.$^6$ .......................... C07C 381/04; C07C 213/00
[52] U.S. Cl. ...................... 564/341; 564/342; 564/346; 564/347; 540/484; 540/544; 540/553; 544/56; 544/582; 544/59; 544/98; 544/106
[58] Field of Search .................. 514/211, 227.5, 514/231.2, 239.5, 571, 717, 913; 540/484, 544, 553; 544/56, 58.2, 59, 98, 106; 564/341, 342, 346, 347

[56] References Cited

U.S. PATENT DOCUMENTS

| | | | |
|---|---|---|---|
| 3,255,241 | 6/1966 | Schultz et al. | 562/431 |
| 3,352,904 | 11/1967 | Bicking et al. | 562/433 |
| 3,419,606 | 12/1968 | Bicking et al. | 562/427 |
| 4,324,782 | 4/1982 | Cragoe | 514/651 |
| 4,390,537 | 6/1983 | Cragoe | 514/239.2 |
| 4,699,926 | 10/1987 | Abraham | 514/680 |
| 4,731,381 | 3/1988 | Abraham et al. | 514/571 |
| 4,731,473 | 3/1988 | Abraham | 562/464 |
| 4,751,244 | 6/1988 | Abraham | 514/563 |
| 4,757,089 | 7/1988 | Epstein | 514/571 |
| 5,352,702 | 10/1994 | Cyrlin | 514/571 |

FOREIGN PATENT DOCUMENTS

| | | |
|---|---|---|
| WO92/16199 | 10/1992 | WIPO. |
| W095/08990 | 4/1995 | WIPO. |

OTHER PUBLICATIONS

Davson, H., *Physiology of the Eye*, 5th Ed., Pergamon Press (1990), pp. 117–122.

Leo, A. J., "Methods of Calculating Partition Coefficients", *Comprehensive Medicinal Chemistry: The Rational Design, Mechanistic Study & Therapeutic Applications of Chemical Compounds*, vol. 4, #18.7, pp. 295–319, Pergamon Press (1990).

Mirrlees, M. S., et al., "Direct Measurement of Octanol–Water Partition Coefficients by High–Pressure Liquid Chromatography", *Journal of Medicinal Chemistry*, vol. 19, No. 5, pp. 615–619 (1976).

Wang, W., et al., "Lipophilicity Influence on Conjunctival Drug Penetration in the Pigmented Rabbit: A Comparison with Corneal Penetration", *Current Eye Research*, vol. 10, No. 6, pp. 571–579 (1991).

Goto, S., et al., "Stability and Serum Albumin Binding of Diuretics in Aqueous Solution", *Yakugaku Zasshi*, vol. 98, pp. 236–240 (1978).

Abraham, D. J., et al., "Design, Synthesis, and Testing of Potential Antisickling Agents. 7. Ethacrynic Acid Analogues", *J. Med. Chem.*, vol. 32, pp. 2460–2467 (1989).

Epstein, D. L., et al., "N–Ethylmalemide Increases the Facility of Aqueous Outflow of Excised Monkey and Calf Eyes", *Invest. Ophthalmol. Vis. Sci.*, vol. 22, pp. 752–756 (1982).

Epstein, D. L., et al., "Influence of Ethacrynic Acid on Outflow Facility in the Monkey and Calf Eye", *Invest. Ophthalmol. Vis. Sci.*, vol. 28, pp. 2067–2075 (1987).

The Assoc. for Research in Vision and Ophthalmology ARVO 1988, No. 24, p. 84: Ozment, et al., "The Effect of Intracameral Ethacrynic Acid on Introcular Pressure of Living Monkeys".

The Assoc. for Research in Vision and Ophthalmology ARVO 1989, Nos. 68 and 70, p. 356: Patel, et al., "Interactions of Ethacrynic Acid and Other Sulfhydryl Agents with Proteins in the Calf Trabecular Meshwork"; Schroeder, et al., Ethacrynic Acid Induced Changes in Cytoskeletal Tubulin.

The Assoc. for Research in Vision and Ophthalmology ARVO 1990, No. 1849, p. 376: Liang, et al., "Ethacrynic Acid Increases Facility of Outflow in the Human Eye In Vitro".

Chemical Abstracts, "N–Argylglycines", Merck & Co., Inc., Neth. Appl. 6,502,404, vol. 64, No. 6, col. 8093 (1966).

Chemical Abstracts, "[[4–(2–Methylenealkanoyl)phenyl]sulfinyl]alkanecarboxylic acids", Merck & Co., Inc., Neth. Appl. 6,506,045, vol. 65, col. 654 (1966).

*Primary Examiner*—José G. Dees
*Assistant Examiner*—Dwayne C. Jones
*Attorney, Agent, or Firm*—Gregg C. Brown; Michael C. Mayo

[57] ABSTRACT

Compounds structurally related to ethacrynic acid are described. The compounds are useful for controlling intraocular pressure. Unlike ethacrynic acid, the compounds of the present invention are capable of effectively penetrating the cornea. Methods of controlling intraocular pressure via topical application of one or more of the compounds to the eye and topical ophthalmic compositions useful in the treatment of glaucoma are also described.

7 Claims, No Drawings

ETHACRYNIC ACID-LIKE COMPOUNDS AND USE THEREOF TO TREAT GLAUCOMA

This is a division, of application Ser. No. 08/049,215, filed Apr. 19, 1993, now U.S. Pat. No. 5,506,226.

BACKGROUND OF THE INVENTION

The present invention relates to certain new compounds believed to be useful in the treatment of glaucoma. The compounds are structurally related to ethacrynic acid, which is a compound having diuretic and anti-allergic properties and which has been described as being useful in the treatment of glaucoma.

Glaucoma is a progressive disease which leads to optic nerve damage, and, ultimately, partial or total loss of vision. The causes of this disease have been the subject of extensive studies for many years, but are still not fully understood. The principal symptom of the disease is an elevated pressure within the eye caused by excess intraocular fluid (i.e., "aqueous humor").

The reasons why the excess fluid accumulates are not fully understood. It is known that the elevated intraocular pressure ("IOP") can be at least partially controlled by administering drugs which affect either the production of aqueous humor within the eye or the flow of aqueous humor out of the eye. The glaucoma therapies currently available primarily involve the use of drugs which act to reduce production of aqueous humor by the ciliary body of the eye. These therapies have been generally effective in the majority of patients. However, it is not always possible to control chronic elevations of IOP by reducing the amount of aqueous humor production, particularly in cases where obstructed outflow of aqueous humor is contributing to the excess of aqueous humor and consequent elevation of IOP. Moreover, the reduction of aqueous humor production creates a risk that the avascular tissues of the eye, particularly the lens and the cornea, will be damaged due to an inadequate supply of nutrients and/or hydration caused by the reduced production of aqueous humor. The possible use of agents which increase the outflow of aqueous humor to control IOP has therefore been a topic of great interest to scientists engaged in glaucoma research.

The use of ethacrynic acid ("ECA") to increase the outflow of aqueous humor has been reported in the literature. This use is described in U.S. Pat. No. 4,757,089 issued to David L. Epstein. The Epstein '089 patent describes a method of increasing aqueous humor outflow by topically administering ECA, or analogs of ECA which are capable of reacting with sulfhydryl groups in the trabecular meshwork of the eye. Epstein postulates that chemical modification of cellular sulfhydryl groups by ECA or ECA analogs alters the egress of aqueous humor from the trabecular meshwork.

Unfortunately, there are serious limitations on the topical ophthalmic use of ECA due to its poor penetration of the cornea. ECA, a carboxylic acid with a pK of 3.5, exists essentially exclusively (greater than 99.9%) in its ionic form, the carboxylate anion, at physiological pH (7.4). Therefore, in spite of the favorable lipophilicity of the neutral species ( calculated log P of 3.19), the species present at physiologic pH, the ionic form, has an extremely unfavorable lipophilicity (experimental log P is −1.15); therefore, the ability of ECA or analogs to penetrate lipophilic corneal membranes at physiological pH is extremely poor. The limited ocular penetration of these acidic compounds severely limits the practical value of ECA in glaucoma therapy, because if the drug can not effectively penetrate the cornea, a therapeutic level of the drug at the postulated site of action (i.e., the trabecular meshwork) will not be achieved.

SUMMARY OF THE INVENTION

The present invention is directed to the provision of certain new compounds considered to be beneficial in the treatment of glaucoma. The compounds are also believed to have anti-allergic properties. The compounds incorporate an amine functionality which has an unusually low pK value, and are capable of penetrating the cornea fairly rapidly, unlike ethacrynic acid. The invention also entails methods of controlling IOP by topically applying one or more of the subject compounds and related compounds to the affected eyes, and associated topical ophthalmic compositions.

DESCRIPTION OF PREFERRED EMBODIMENTS

The compounds utilized in the present invention have the following structure:

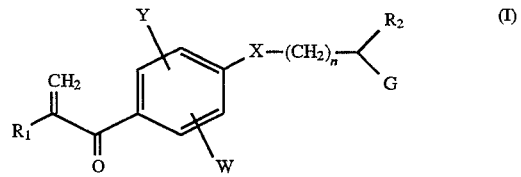

wherein:

X is O, S or $SO_m$, wherein m is 1 or 2;

n is 0, 1 or 2;

W and Y are independently selected from hydrogen, halogen (F, Cl, Br), alkyl($C_{1-4}$), alkoxy($C_{1-4}$), or alkyl ($C_{1-3}$) substituted by one or more fluorine atoms;

$R_1$ is alkyl($C_{1-4}$), straight chain or branched, and may be substituted with one or more of alkoxy($C_{1-4}$), alkoxycarbonyl($C_{1-5}$), halogen (F, Cl, Br), or $NR_3R_4$;

$R_2$ is hydrogen, lower alkyl ($C_{1-4}$), hydroxymethyl, alkoxy($C_{1-4}$)methyl, alkoxy($C_{1-4}$)alkoxy($C_{2-4}$)methyl, or hydroxyalkoxy($C_{2-4}$)methyl;

G is $NR_3R_4$, alkyl($C_{1-4}$) or hydrogen, or G and $R_2$ together with the intervening carbon atom may be incorporated into a saturated heterocyclic ring of the following structure:

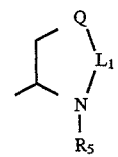

wherein Q, $L_1$, and $R_5$ are as defined below;

$R_3$ and $R_4$ are independently selected from hydrogen, alkyl ($C_{1-6}$), alkenyl ($C_{3-8}$), or alkynyl ($C_{3-8}$), straight chain or branched, and may be substituted with one or more of halogen (F, Cl, Br), hydroxyl, alkoxy($C_{1-4}$), alkyl ($C_{1-4}$)sulfone, or alkoxycarbonyl($C_{1-5}$), provided that $R_3$ and $R_4$ cannot both be hydrogen; or $R_3$ and $R_4$ together with the nitrogen atom of the $NR_3R_4$ group may be incorporated into a saturated heterocyclic ring selected from:

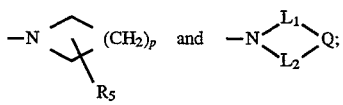

p is 1–4;

$L_1$ and $L_2$ are independently chosen from —$(CH_2)_q$—, wherein q is 2 or 3, or —$CHR_7CH_2$—;

Q is O, $NR_6$, S or $SO_2$;

$R_5$ is hydrogen, alkyl ($C_{1-4}$), alkoxy ($C_{1-3}$), alkoxy($C_{1-3}$)alkyl($C_{2-4}$), alkoxycarbonyl($C_{1-5}$) or hydroxyalkyl ($C_{1-3}$);

$R_6$ is hydrogen, hydroxyalkyl($C_{2-4}$), alkoxy($C_{1-3}$)alkyl ($C_{2-4}$), alkyl($C_{2-4}$)carbonyl or alkyl($C_{1-3}$)sulfonyl; and $R_7$ is alkyl($C_{1-4}$), alkoxy($C_{1-3}$), alkoxycarbonyl($C_{1-5}$) or hydroxyalkyl($C_{1-3}$), provided that at least one but not both of $R_1$ and G include an amine functionality.

The invention also encompasses pharmaceutically acceptable salts of the above-identified compounds. The compounds may exist in isomeric form, so the use of pure isomers of the compounds is comtemplated, as well as the use of racemic mixtures of the isomers.

Certain compounds of formula (I), wherein X is O, are known. See, for example, U.S. Pat. Nos. 4,342,782 and 4,390,537; the entire contents of the foregoing patents are hereby incorporated in the present specification by reference.

The compounds of the present invention can be prepared by one skilled in the art of organic chemistry by the general synthetic procedures described in U.S. Pat. No. 4,342,782 or modifications thereof, such as the procedures illustrated in Equations 1 and 2 below, wherein $R_1$, W, Y, $R_2$, and G are as described above, and X is halogen (chloride, bromide or iodide):

Equation 1

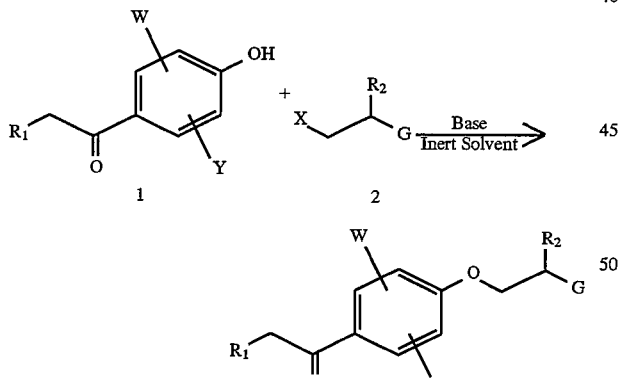

Equation 2

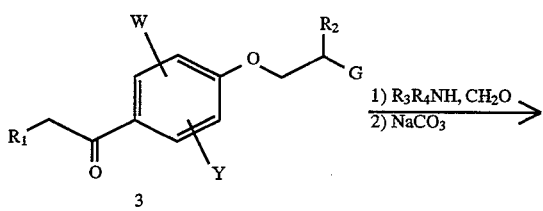

-continued
Equation 1

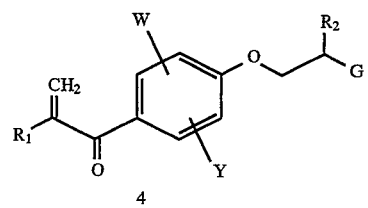

That is, the desired phenolic ketones 1 can be alkylated with an appropriately substituted alkyl halide 2 using a suitable base, such NaH, KOH, DBU or the like, in a compatible inert solvent to provide the intermediate ethers 3. These intermediate ethers can be converted into the desired α-methylene ketones 4 by initial reaction with formaldehyde and a secondary amine, such as dimethylamine, to give the so-called Mannich salt, which can be readily dehydroaminated upon treatment with weak base, such as sodium carbonate.

Compounds of formula (I) wherein X is $SO_2$ can be prepared as illustrated in Equation 3 below:

Equation 3

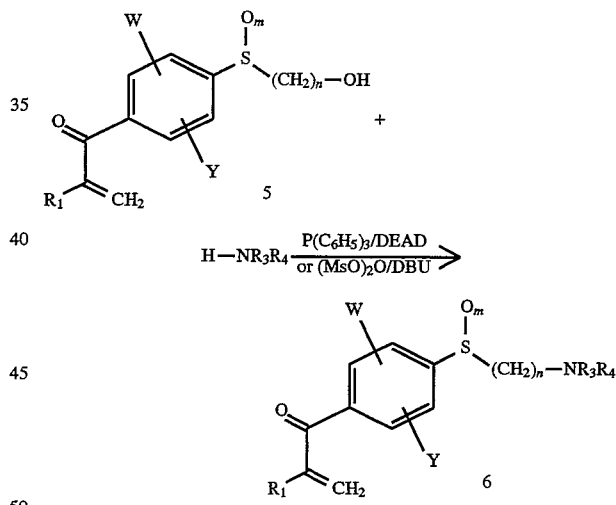

The desired intermediates 5 can be prepared from the requisite aniline by procedures described in Netherlands Patent Application 6,506,045 or modifications thereof. Incorporation of the desired amino group to provide compounds 6 can be accomplished by procedures known in the art, but peferably by displacement of an aryl or alkyl sulfonate ester under mildly basic conditions, or by using conditions of the Mitsunobu reaction, diethyl azodicarboxylate-triphenylphosphine.

Preferred compounds of formula (I) are those wherein G is $NR_3R_4$. Particularly preferred are the following compounds:

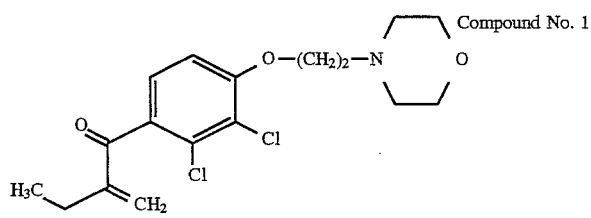

1-[2,3-Dichloro-4-[2-(4-morpholinyl)ethoxy]phenyl]-
2-methylene-1-butanone;

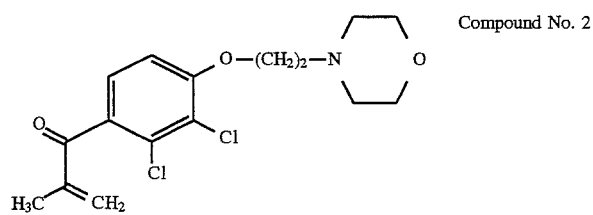

1-[2,3-Dichloro-4-[2-(4-morpholinyl)ethoxy]phenyl]-2-
methylene-1-propanone;

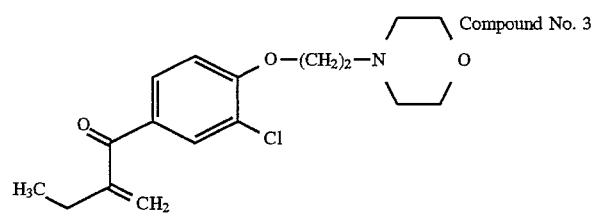

1-[3-Chloro-4-[2-(4-morpholinyl)ethoxy]phenyl]-2-
methylene-1-butanone;

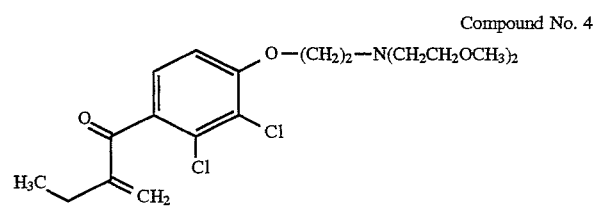

1-[2,3-Dichloro-4-[2-[bis(2-methoxyethyl)amino]ethoxy]phenyl]-2-
methylene-1-butanone;

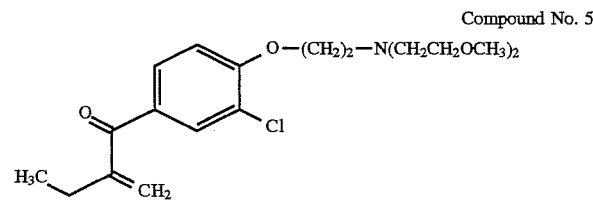

1-[3-Chloro-4-[2-[bis(2-methoxyethyl)amino]ethoxy]phenyl]-2-
methylene-1-butanone;

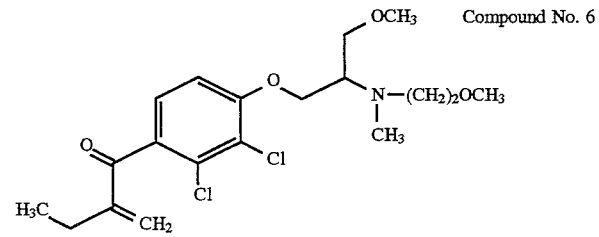

1-[2,3-Dichloro-4-[3-methoxy-2-
[(2-methoxyethyl)methylamino]propoxy]phenyl]-2-
methylene-1-butanone;

-continued

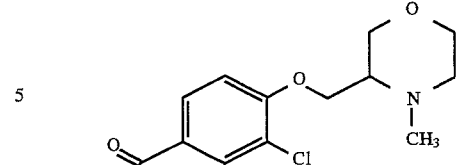

1-[2,3-Dichloro-4-[(4-methyl-3-morpholinyl)methoxy]phenyl]-2-
methylene-1-butanone;

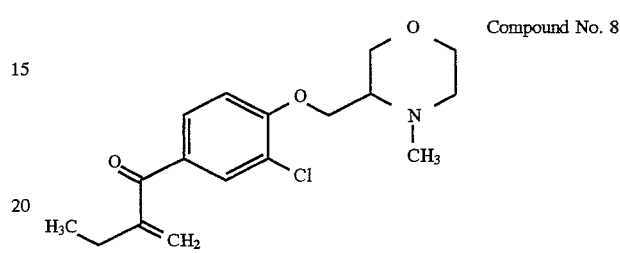

1-[3-Chloro-4-[(4-methyl-3-morpholinyl)methoxy]phenyl]-2-
methylene-1-butanone;

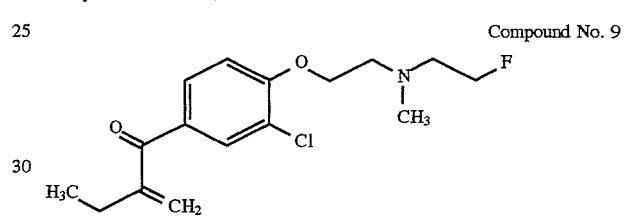

1-[3-Chloro-4-[(2-(2-fluoroethyl)methylamino)ethoxy]phenyl]-2-
methylene-1-butanone;

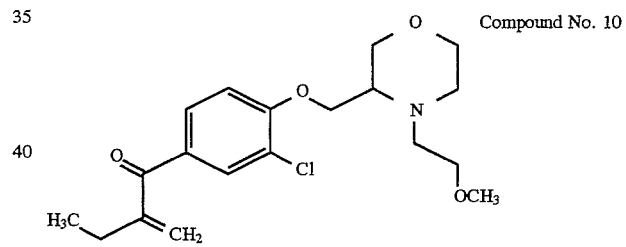

1-[3-Chloro-4-[(4-(2-methoxyethyl)-3-morpholinyl)methoxy]phenyl]-2-
methylene-1-butanone;

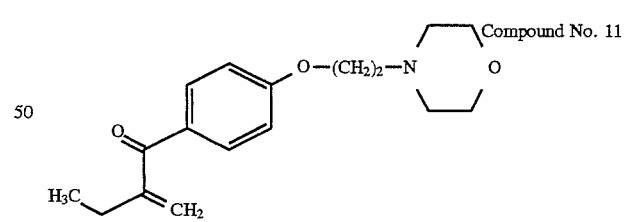

1-[4-[2-(4-Morpholinyl)ethoxy]phenyl]-2-
methylene-1-butanone;

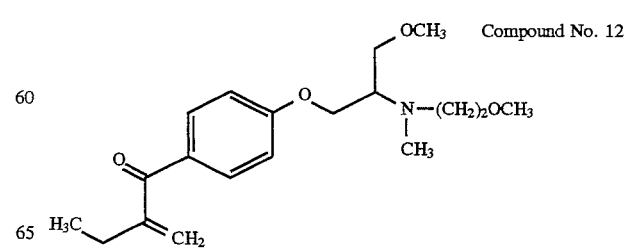

-continued

1-[4-[3-methoxy-2-[(2-methoxyethyl)methylamino]propoxy]phenyl]-2-methylene-1-butanone;

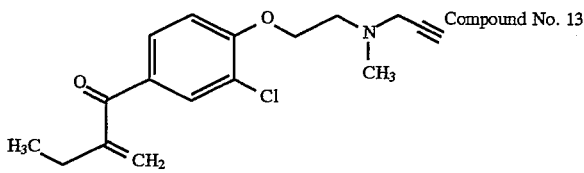

Compound No. 13

1-[3-Chloro-4-[2-[(1-propyn-3-yl)methylamino]ethoxy]phenyl]-2-methylene-1-butanone;

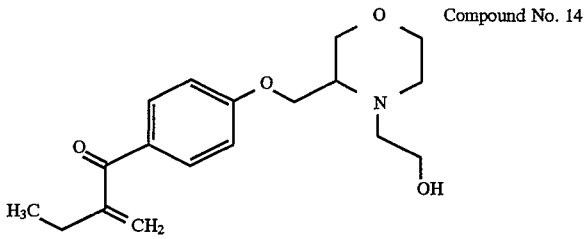

Compound No. 14

1-[4-[(4-(2-Hydroxyethyl)-3-morpholinyl)methoxy]phenyl]-2-methylene-1-butanone.

In order to be therapeutically effective, agents applied topically to the eye must be able to traverse the external surfaces of the eye, principally the cornea but also of interest are the sclera and conjunctiva, in order to reach their target tissues. As pointed out by Daveson (Physiology of the Eye, $5^{th}$ ed., p. 118, Pergamon, 1990), lipid-soluble substances are expected to, and indeed have been shown to, readily pass into the membranes of the cornea because they easily pass into the lipid membranes of the cells while lipid insoluble substances penetrate the cornea with difficulty. Therefore, for a substance which is an organic acid, the degree of dissociation is an important consideration; similarly, for a substance which is an organic base, the degree of formation of the conjugate acid is an equally important consideration, since for either type of substance the penetration of the cornea by the more lipophilic unionized species is more rapid than that of the ion. The major role of lipophilicity in affecting drug penetration of the cornea and conjunctiva has been demonstrated for a variety of classes of therapeutic agents when applied topically to the eye. See, for example, W. Wang, et al, Current Eye Research, 10, 571 (1991) and references cited therein.

A measure of the ability of a substance to associate with lipid environments can be ascertained from the extent of its partitioning between two immiscible liquid phases. This value, the partition coefficient or distribution coefficient, can be determined experimentally using, for example, water and n-octanol as the liquid phases; there is considerable literature available concerning these methods; see, for example, W. J. Dunn, III, J. Block and R. S. Pearlman, eds., *Partition Coefficient: Determination and Estimation*, Pergamon Press, 1986, and M. S. Mirrlees, et al., *J. Med. Chem*, 19, 615 (1976). However, because of the time consuming nature of these experimental determinations and as a means to estimate the partitioning characteristics of compounds which are either not available or have not yet been prepared, empirical procedures have been developed for calculating partition coefficients. One such approach which has received wide acceptance is the CLOGP algorithm developed by the Pomona College Medicinal Chemistry Project. For a discussion of this application, see Leo in "Comprehensive Medicinal Chemistry", Vol. 4, p. 295. This procedure has been used for estimating the partition coefficients for representative compounds of formula (I).

A basic premise of the present invention is that compounds of formula (I) do not contain a carboxylic acid functionality as a structural element, but do have incorporated into their structure an amine functionality which has an unusually low pK value, e.g., 5.4–7.4, either within group G or $R_1$, in formula (I), but not both. The acid salt forms of these compounds will be highly soluble under mildly acidic conditions, conditions which are desirable for enhanced stability of the crucial α-methylene-ketone moiety of these compounds, and furthermore these conditions are acceptable for ocular formulations. At physiological pH, however, the compounds of this invention will exist primarily in the free base form (non-charged species); this neutral species will have a reduced solubility compared to the charged species, but will be significantly more lipophilic than the charged species, a property which will facilitate rapid transport through the lipophilic corneal membranes, thus allowing the compounds to gain access to the target tissue, the trabecular meshwork. That is, the cationic form of the compounds of this invention which would be present in mildly acidic formulations will upon topical administration to the eye be transformed to the neutral free base form under the physiological conditions of the tear film. The lipophilic neutral compounds will cross the cornea more readily than the anionic form of ethacrynic acid present at physiological pH. The physiochemical properties of the compounds of the present invention are further illustrated by the data presented in the following table:

| Compound | Calculated Log P CLOGP | Calculated pK | Estimated Neutral Species at pH 7.4 (%) |
|---|---|---|---|
| 3 | 3.51 | 6.3 | 92.6 |
| 6 | 3.08 | 6.1 | 95.2 |
| 9 | 2.60 | 5.5 | 98.7 |
| 10 | 2.90 | 6.0 | 96.2 |
| 11 | 3.01 | 6.4 | 90.9 |
| 12 | 2.71 | 6.2 | 94.1 |
| 13 | 2.60 | 5.5 | 98.7 |
| 14 | 2.42 | 5.5 | 98.7 |

Another premise of the present invention is that a compound which maintains an acceptable level of reactivity toward physiologically relevant nucleophiles (most probably specific protein mercapto groups) while displaying an acceptable level of solubility will be therapeutically useful in the treatment of ocular hypertension. It is further maintained that the carboxylic acid group present in ethacrynic acid is not a requirement for eliciting the desired response, and that this group can be replaced as indicated above.

Due to their improved aqueous solubility at acceptable formulation pH values (i.e., 4.7 to 6.0) and their acceptable lipophilicity at physiological pH, the compounds of formula (I) will readily gain access to the target tissue, the trabecular meshwork cells, following topical administration to the eye. The exact dosage regimen may be determined by clinicians. In general, an ophthalmic composition containing one or more of the compounds of formula (I) will be applied to the eye one to four times per day, perferably one to two times per day. The dosage will be an amount effective to achieve the therapeutic objectives of lowering elevated intraocular pressure or controlling intraocular pressure so as to prevent such elevations. Such an amount will be referred to herein as "a therapeutically effective amount".

The compounds of formula (I) may be incorporated in various types of ophthalmic compositions, in accordance with formulation techniques known to those skilled in the art. As these compounds are relatively soluble in water, aqueous formulations, particularly solutions, are preferred. The compounds will be contained in such compositions in an amount effective to control elevations of intraocular pressure; such amount will generally be in the range of from about 0.01 to about 5 percent by weight, based on the total weight of the composition ("wt. %"), and preferably from about 0.1 to about 1 wt. %.

The compositions may contain one or more chemical preservatives to prevent microbial contamination of the compositions when dispensed in multiple dose containers. Preservatives which may be employed include benzalkonium chloride, thimerosal, chlorobutanol, methyl paraben, propyl paraben, phenylethyl alcohol, edetate disodium, sorbic acid, and other agents known to those skilled in the art. Such preservatives are typically employed at a level of from about 0.001 to 1.0 wt. %. The compositions may also contain one or more buffering agents to maintain the pH of the compositions at or near the physiological pH of 7.4. Examples of buffering agents which may be utilized include phosphates, borates, citrates and carbonates. The tonicity of the compositions will preferably be at or near the tonicity of human tears (i.e., approximately 300–320 milliosmoles). The tonicity of the compositions can be adjusted, as needed, by adding sodium chloride, mannitol or other conventional and well-known agents. It may also be desirable to adjust the viscosity of the compositions, so as to improve the comfort of the compositions when topically applied to the eye. Viscosity-building agents which may be utilized include polyvinyl alcohol, tyloxapol, methylcellulose, hydroxypropyl methylcellulose, polyvinyl pyrrolidone, carboxyvinyl polymers, and various other agents known to those skilled in the art.

What is claimed is:

1. A compound of the formula:

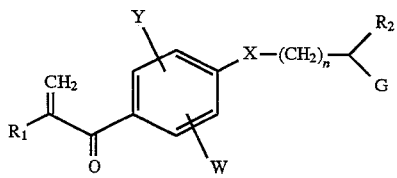

wherein:

X is $SO_m$, and m is 1 or 2;

n is 0, 1 or 2;

W and Y are independently selected from hydrogen, halogen, alkyl($C_{1-4}$), alkoxy($C_{1-4}$), or alkyl($C_{1-3}$) substituted by one or more fluorine atoms;

$R_1$ is alkyl($C_{1-4}$), straight chain or branched, and may be substituted with one or more of alkoxy($C_{1-4}$), alkoxycarbonyl($C_{1-5}$), halogen or $NR_3R_4$;

$R_2$ is hydrogen, lower alkyl ($C_{1-4}$), hydroxymethyl, alkoxy($C_{1-4}$)methyl, alkoxy($C_{14}$)alkoxy($C_{2-4}$)methyl, or hydroxyalkoxy($C_{2-4}$)methyl;

G is $NR_3R_4$, alkyl($C_{1-4}$) or hydrogen, or G and $R_2$ together with the intervening carbon atom may be incorporated into a saturated heterocyclic ring of the following structure:

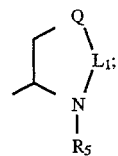

$R_3$ and $R_4$ are independently selected from hydrogen, alkyl ($C_{1-6}$), alkenyl ($C_{3-8}$), or alkynyl ($C_{3-8}$), straight chain or branched, and may be substituted with one or more of halogen, hydroxyl, alkoxy($C_{1-4}$), alkyl($C_{1-4}$) sulfone, or alkoxycarbonyl($C_{1-5}$), provided that $R_3$ and $R_4$ cannot both be hydrogen; or $R_3$ and $R_4$ together with the nitrogen atom may be incorporated into a saturated heterocyclic ring selected from:

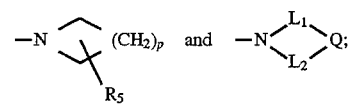

p is 1–4;

$L_1$ and $L_2$ are independently chosen from —$(CH_2)_q$—, wherein q is 2 or 3, or —$CHR_7CH_2$—;

Q is O, $NR_6$, S or $SO_2$;

$R_5$ is hydrogen, alkyl ($C_{1-4}$), alkoxy ($C_{1-3}$), alkoxy($C_{1-3}$)alkyl($C_{2-4}$), alkoxycarbonyl($C_{1-5}$) or hydroxyalkyl ($C_{1-3}$);

$R_6$ is hydrogen, hydroxyalkyl($C_{2-4}$), alkoxy($C_{1-3}$)alkyl ($C_{2-4}$), alkyl($C_{2-4}$)carbonyl or alkyl($C_{1-3}$)sulfonyl; and $R_7$ is alkyl($C_{1-4}$), alkoxy($C_{1-3}$), alkoxycarbonyl($C_{1-5}$) or hydroxyalkyl($C_{1-3}$);

provided that $R_1$ is $NR_3R_4$ when G is alkyl($C_{1-4}$) or hydrogen, and $R_1$ can not be $NR_3R_4$ when G is not alkyl ($C_{1-4}$) or hydrogen; or a pharmaceutically acceptable salt thereof.

2. A compound according to claim 1, wherein G is $NR_3R_4$.

3. An ophthalmic composition comprising an amount of a compound of the following formula effective to control intraocular pressure:

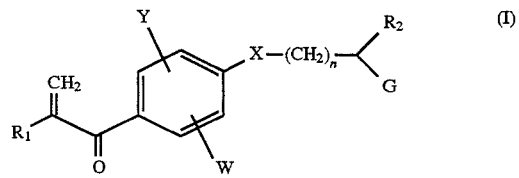

wherein:

X is O, S, or $SO_m$, and m is 1 or 2;

n is 0, 1 or 2;

W and Y are independently selected from hydrogen, halogen, alkyl($C_{1-4}$), alkoxy($C_{1-4}$), or alkyl($C_{1-3}$) substituted by one or more fluorine atoms;

$R_1$ is alkyl($C_{1-4}$), straight chain or branched, and may be substituted with one or more of alkoxy($C_{1-4}$), alkoxycarbonyl($C_{1-5}$), halogen or $NR_3R_4$;

$R_2$ is hydrogen, lower alkyl($C_{1-4}$), hydroxymethyl, alkoxy($C_{1-4}$)methyl, alkoxy($C_{14}$)alkoxy($C_{2-4}$)methyl, or hydroxyalkoxy($C_{2-4}$)methyl;

G is $NR_3R_4$, alkyl($C_{1-4}$) or hydrogen, or G and $R_2$ together with the intervening carbon atom may be incorporated into a saturated heterocyclic ring of the following structure:

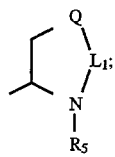

$R_3$ and $R_4$ are independently selected from hydrogen, alkyl ($C_{1-6}$), alkenyl ($C_{3-8}$), or alkynyl($C_{3-8}$), straight chain or branched, and may be substituted with one or more of halogen, hydroxyl, alkoxy($C_{1-4}$), alkyl($C_{1-4}$) sulfone, or alkoxycarbonyl($C_{1-5}$), provided that $R_3$ and $R_4$ cannot both be hydrogen; or $R_3$ and $R_4$ together with the nitrogen atom may be incorporated into a saturated heterocyclic ring selected from:

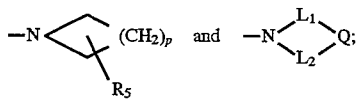

p is 1–4;

$L_1$ and $L_2$ are independently chosen from —$(CH_2)_q$—, wherein q is 2 or 3, or —$CHR_7CH_2$—;

Q is O, $NR_6$, S or $SO_2$;

$R_5$ is hydrogen, alkyl ($C_{1-4}$), alkoxy ($C_{1-3}$), alkoxy($C_{1-3}$)alkyl($C_{2-4}$), alkoxycarbonyl($C_{1-5}$) or hydroxyalkyl ($C_{1-3}$);

$R_6$ is hydrogen, hydroxyalkyl($C_{2-4}$), alkoxy($C_{1-3}$)alkyl ($C_{2-4}$), alkyl($C_{2-4}$)carbonyl or alkyl($C_{1-3}$)sulfonyl; and $R_7$ is alkyl($C_{1-4}$), alkoxy($C_{1-3}$), alkoxycarbonyl($C_{1-5}$) or hydroxyalkyl($C_{1-3}$);

provided that $R_1$ is $NR_3R_4$ when G is alkyl($C_{1-4}$) or hydrogen, and $R_1$ can not be $NR_3R_4$ when G is not alkyl ($C_{1-4}$) or hydrogen; or a pharmaceutically acceptable salt thereof, and a pharmaceutically acceptable vehicle therefor.

4. A composition according to claim 3, wherein X is O.

5. A composition according to claim 3, wherein X is $SO_m$.

6. A composition according to claim 3, wherein G is $NR_3R_4$.

7. A composition according to claim 3, wherein the compound is selected from the group consisting of:

1-[2,3-Dichloro-4-[2-(4-morpholinyl)ethoxy]phenyl]-2-methylene-1-butanone;

1-[2,3-Dichloro-4-[2-(4-morpholinyl)ethoxy]phenyl]-2-methylene-1-propanone;

1-[3-Chloro-4-[2-(4-morpholinyl)ethoxy]phenyl]-2-methylene-1-butanone;

1-[2,3-Dichloro-4-[2-[bis(2-methoxyethyl)amino]ethoxy]phenyl]-2-methylene-1-butanone;

1-[3-Chloro-4-[2-[bis(2-methoxyethyl)amino]ethoxy]phenyl]-2-methylene-1-butanone;

1-[2,3-Dichloro-4-[3-methoxy-2-[(2-methoxyethyl)methylamino]propoxy]phenyl]-2-methylene-1-butanone;

1-[2,3-Dichloro-4-[(4-methyl-3-morpholinyl)methoxy]phenyl]-2-methylene-1-butanone;

1-[3-Chloro-4-[(4-methyl-3-morpholinyl)methoxy]phenyl]-2-methylene-1-butanone;

1-[3-Chloro-4-[(2-(2-fluoroethyl)methylamino)ethoxy]phenyl]-2-methylene-1-butanone;

1-[3-Chloro-4-[(4-(2-methoxyethyl)-3-morpholinyl)methoxy]phenyl]-2-methylene-1-butanone;

1-[4-[2-(4-Morpholinyl)ethoxy]phenyl]-2-methylene-1-butanone;

1-[4-[3-methoxy-2-[(2-methoxyethyl)methylamino]propoxy]phenyl]-2-methylene-1-butanone;

1-[3-Chloro-4-[2-[(1-propyn-3-yl)methylamino]ethoxy]phenyl]-2-methylene-1-butanone; and 1-[4-[(4-(2-Hydroxyethyl)-3-morpholiny)methoxy]phenyl]-2-methylene-1-butanone.

* * * * *